(12) United States Patent
Saha et al.

(10) Patent No.: US 10,909,684 B2
(45) Date of Patent: Feb. 2, 2021

(54) SYSTEMS AND METHODS FOR AIRWAY TREE SEGMENTATION

(71) Applicant: University of Iowa Research Foundation (UIRF), Iowa City, IA (US)

(72) Inventors: Punam Kumar Saha, Coralville, IA (US); Eric A. Hoffman, Iowa City, IA (US); Syed Ahmed Nadeem, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 77 days.

(21) Appl. No.: 16/195,610

(22) Filed: Nov. 19, 2018

(65) Prior Publication Data

US 2019/0180442 A1 Jun. 13, 2019

Related U.S. Application Data

(60) Provisional application No. 62/588,671, filed on Nov. 20, 2017, provisional application No. 62/588,693, filed on Nov. 20, 2017.

(51) Int. Cl.
*G06T 7/11* (2017.01)
*A61B 6/03* (2006.01)
(Continued)

(52) U.S. Cl.
CPC ............... *G06T 7/11* (2017.01); *A61B 6/032* (2013.01); *A61B 6/466* (2013.01); *A61B 6/5211* (2013.01);
(Continued)

(58) Field of Classification Search
CPC combination set(s) only.
See application file for complete search history.

(56) References Cited

U.S. PATENT DOCUMENTS

| 10,600,185 B2* | 3/2020 | Yang | G06T 7/187 |
| 2014/0094691 A1* | 4/2014 | Steinberg | A61B 5/061 |
| | | | 600/424 |

(Continued)

OTHER PUBLICATIONS

Bram van Ginneken et al, "Robust Segmentation and Anatomical Labeling of the Airway Tree from Thoracic CT Scans", D. Metaxes et al, (EDS.): MICCAI 2008, Part, I, LNCS 5241, pp. 219-226.
(Continued)

*Primary Examiner* — Tsung Yin Tsai
(74) *Attorney, Agent, or Firm* — Blank Rome LLP

(57) ABSTRACT

Novel systems and methods for airway segmentation are disclosed using confident airway volume, multi-scale topological and geometric leakage detection, exact leakage localization and correction, forbidden volume insertion and freezing, iterative shift in growing techniques starting with a conservative parameter/strategy and progressing toward generous ones, and a final pruning using machine learning, neural network, deep learning or artificial intelligence methods. The systems and methods are fully automated requiring no manual inputs or post-editing steps. The systems and methods use region growing-based segmentation to iteratively grow an airway tree starting with an initial seed, possibly inside the trachea, and a conservative segmentation parameter, e.g., a conservative threshold value for intensity-based region growing. The method then gradually progresses toward more generous values of the segmentation parameters until there is convergence.

24 Claims, 12 Drawing Sheets

(51) Int. Cl.
*A61B 6/00* (2006.01)
*G06T 7/187* (2017.01)
*G06T 7/00* (2017.01)

(52) U.S. Cl.
CPC ............ *G06T 7/187* (2017.01); *G06T 7/0012* (2013.01); *G06T 2207/10081* (2013.01); *G06T 2207/20016* (2013.01); *G06T 2207/20072* (2013.01); *G06T 2207/20076* (2013.01); *G06T 2207/20081* (2013.01); *G06T 2207/30061* (2013.01); *G06T 2207/30172* (2013.01)

(56) References Cited

U.S. PATENT DOCUMENTS

| | | | | |
|---|---|---|---|---|
| 2015/0150457 | A1* | 6/2015 | Wu | A61B 5/445 600/425 |
| 2015/0227809 | A1* | 8/2015 | Alpert | G06K 9/4628 382/132 |
| 2015/0238270 | A1* | 8/2015 | Raffy | A61B 5/7275 600/407 |
| 2016/0110632 | A1* | 4/2016 | Kiraly | G06K 9/342 382/128 |
| 2017/0156582 | A1* | 6/2017 | Ehlers | G06T 7/0012 |
| 2018/0000441 | A1* | 1/2018 | Wang | G06T 5/30 |
| 2018/0108139 | A1* | 4/2018 | Abramoff | G06N 3/0454 |
| 2018/0143199 | A1* | 5/2018 | Liu | A61B 5/055 |
| 2019/0090951 | A1* | 3/2019 | Camus | A61B 8/483 |
| 2019/0099159 | A1* | 4/2019 | Voigt | G06T 7/60 |

OTHER PUBLICATIONS

Nizar N. Jarjour et al. "Severe Asthma—Lessons Learned from the National Heart, Lung, and Blood Institute Severe Asthma Research Program"; AM J Respir Crit CareMed vol. 185, Iss.4, pp. 356-362, Feb. 15, 2012.

Harvey O. Coxson et al., Using Pulmonary Imaging to Move Chronic Obstructive Pulmonary Disease beyond $FEV_1$; Am J Respir Crit Care Med. vol. 190, Iss 2, pp. 135-144, Jul. 15, 2014.

P.K. Saha et al., "3D Digital Topology under Binary Transformation with Applications"; Computer Vision and Image Understanding; vol. 63, No. 3, May, pp. 418-429, 1996; Article No. 0032.

Yinxiao Liu et al., "A Robust Algorithm for Thickness Computation at Low Resolution and Its Application to In Vivo Trabecular Bone CT Imaging"; IEEE Transaction on Biomedical Engineering, vol. 61, No. 7, Jul. 2014, pp. 2057-2069.

Kálmán Palágyi, "A Sequential 3D Curve-Thinning Algorithm Bases on Isthmuses"; G. Bebis et al. (Eds.): ISVC 2014, Part II, LNCS 8888, pp. 406-415, 2014.

John D. Newell, Jr. et al., "Development of Quantitative CT Lung Protocols"; *J Thorac Imaging*, Sep. 2013; 28(5).

Dakai Jin et al., "Filtring Non-Significant Quench Points Using Collision Impact in Grassfire Propagation"; V. Murino and E. Puppo (Eds.): ICIAP 2015, Part I, LNCS 9279, pp. 432-443, 2015.

Punam K. Saha et al. "Fuzzy Distance Transform: Theory, Algorithms, and Applications"; Computer Vison and Image Understanding 86, 171-190 (2002).

Juerg Tschirren et al. "Intrathoracic Airway Trees: Segmentation and Airway Morphology Analysis From Low-Dose CT Scans", IEEE Transactions on Medical Imaging, vol. 24, No. 12, Dec. 2005, pp. 1529-1539.

Mario Castro, MD, MPH, et al., "Lung imaging in asthmatic patients: The picture is clearer"; 2011 American Academy of Allergy, Asthma & Immunology, pp. 467-478.

Jerg Tschirren et al., "Matching and Anatomical Labeling of Human Airway Tree"; IEEE Transactions on Medical Imaging, vol. 24, No. 12, Dec. 2005, pp. 1540-1547.

Elizabeth Bullitt et al., "Measuring Tortuosity of the Intracerebral Vasculature from MRA Images"; IEEE Transactions on Medical Imaging, vol. 22, No. 9, Sep. 2003, pp. 1163-1171.

Eric A. Hoffman et al., "Pulmonary CT and MRI Phenotypes that help explain COPD Pathophysiology and Outcomes", *J Magn Reson Imaging*, Mar. 2016; 43(3): 544-557.

Kensaku Mori et al., "Recognition of Bronchus in Three-Dimensional X-ray CT Images with Applications to Virtualized Bronchoscopy System", Proceedings of ICPR '96; pp. 528-532.

* cited by examiner

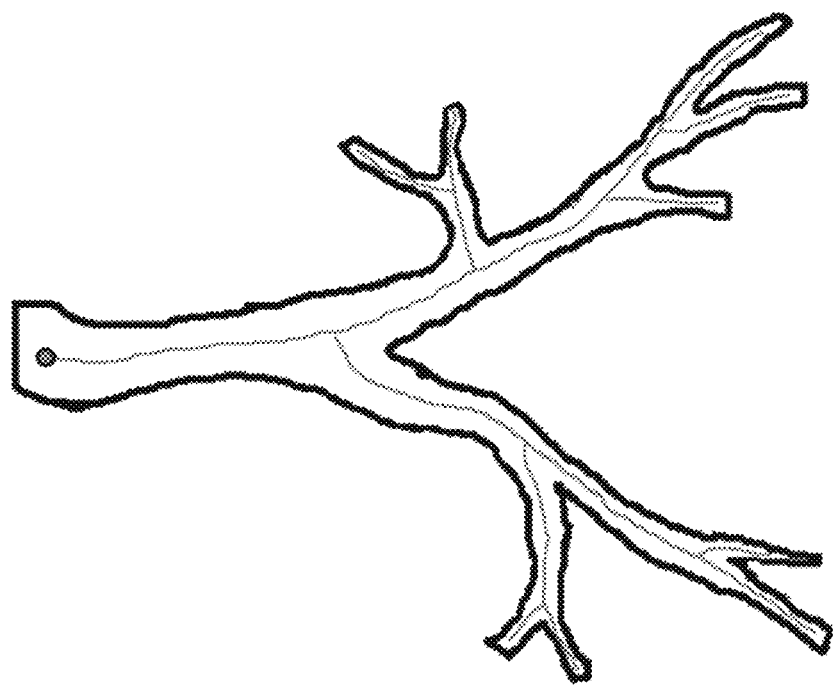
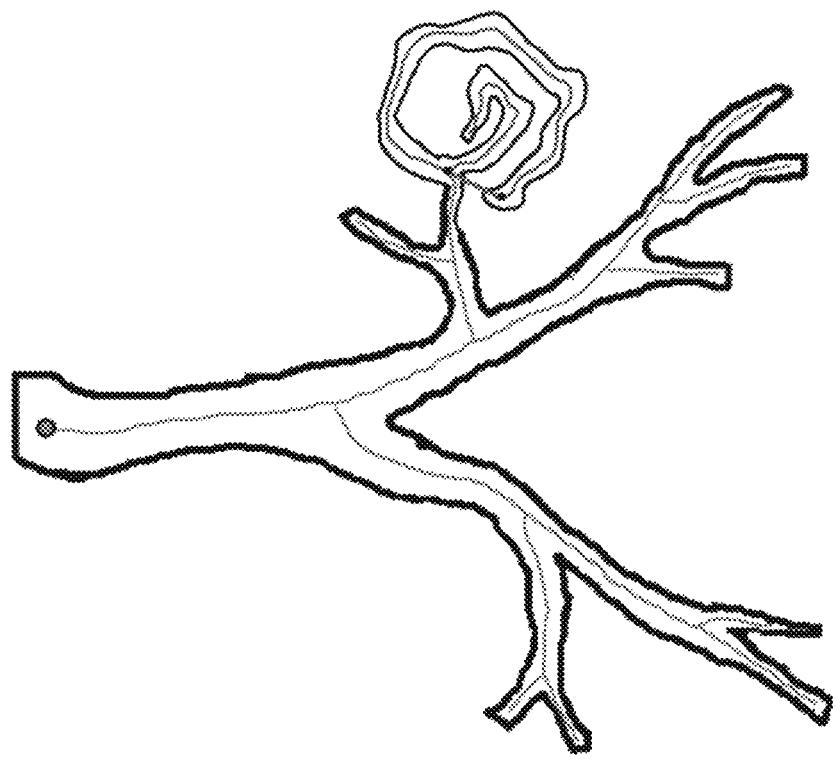

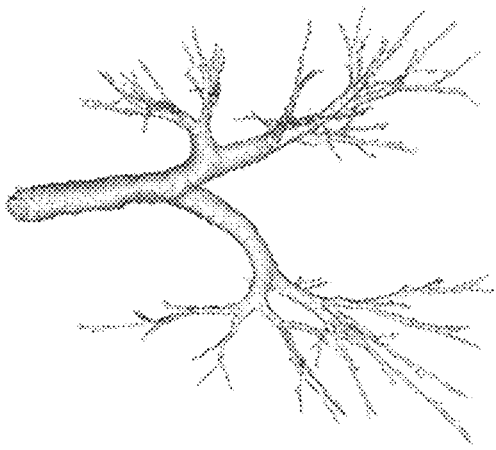
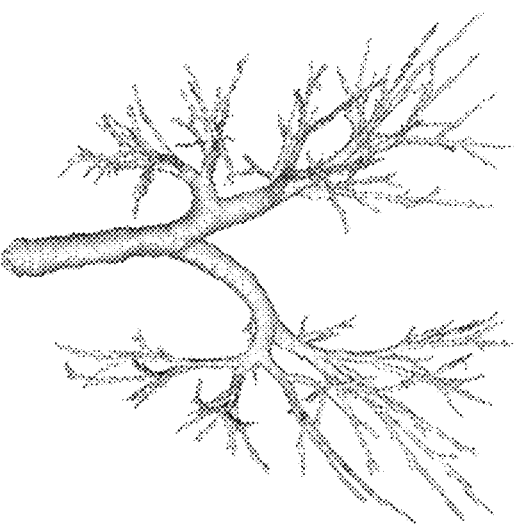
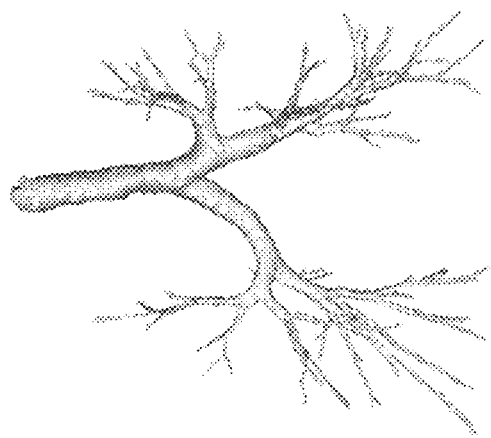
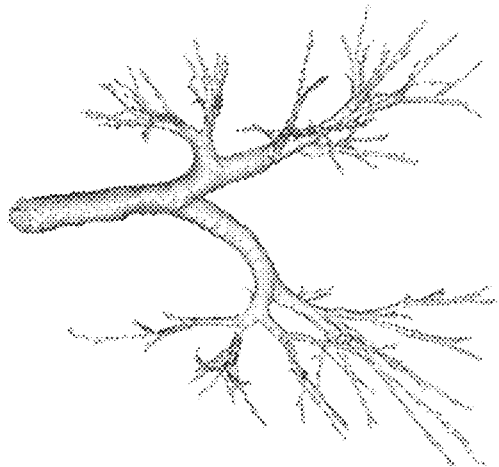

SYSTEMS AND METHODS FOR AIRWAY TREE SEGMENTATION

CROSS-REFERENCE TO RELATED APPLICATIONS

This application claims the benefit of U.S. Provisional App. Nos. 62/588,671 and 62/588,693, both filed on Nov. 20, 2017, the entire contents of both of which are hereby incorporated by reference.

STATEMENT OF FEDERALLY SPONSORED RESEARCH OR DEVELOPMENT

This invention was made with government support under R01 HL1 12986 awarded by the National Institutes of Health. The government has certain rights in the invention.

FIELD OF THE INVENTION

The present invention relates to systems and methods that utilize automated algorithms for Computed Tomography (CT)-based segmentation of airways.

BACKGROUND OF THE INVENTION

There is a growing use of quantitative computed tomography (QCT) to assess the lung both in terms of parenchymal characteristics as well as characteristics of the bronchial tree. M. Castro et al., "Lung imaging in asthmatic patients: the picture is clearer," *Journal of Allergy and Clinical Immunology*, vol. 128, no. 3, pp. 467-478, 2011; N. N. Jarj our et al., "Severe asthma: lessons learned from the national heart, lung, and blood institute severe asthma research program," *American journal of respiratory and critical care medicine*, vol. 185, no. 4, pp. 356-362, 2012; J. D. Newell Jr, J. Sieren, and E. A Hoffman, "Development of quantitative CT lung protocols," *Journal of thoracic imaging*, vol. 28, no. 5, 2013; H. O. Coxson, J. Leipsic, G. Parraga, and D. D. Sin, "Using pulmonary imaging to move chronic obstructive pulmonary disease beyond FEV1," *American journal of respiratory and critical care medicine*, vol. 190, no. 2, pp. 135-144, 2014; E. A Hoffman, D. A Lynch, R. G. Barr, E. J. van Beek, and G. Parraga, "Pulmonary CT and MM phenotypes that help explain chronic pulmonary obstruction disease pathophysiology and outcomes," *Journal of Magnetic Resonance Imaging*, vol. 43, no. 3, pp. 544-557, 2016.

The labeling of the extracted airway tree allows for comparison of spatially matched airway segments across individuals. These comparisons can provide new insights into airway phenotypes. J. Tschirren, E. A Hoffman, G. McLennan, and M. Sonka, "Intrathoracic airway trees: segmentation and airway morphology analysis from low-dose CT scans," *IEEE transactions on medical imaging*, vol. 24, no. 12, pp. 1529-1539, 2005; J. Tschirren, G. McLennan, K. Palagyi, E. A Hoffman, and M. Sonka, "Matching and anatomical labeling of human airway tree," *IEEE transactions on medical imaging*, vol. 24, no. 12, pp. 1540-1547, 2005.

The various methods and systems that have been used to study airways suffer from a lack of accuracy due to poor image data processing and often require human intervention. These problems lead to variability in the data. To our knowledge, there have been no fully automated methods developed for airway tree segmentation out to two generations beyond the segmental airways free of the need for user review that assure that the airway tree has been extracted appropriately.

Described herein are novel systems and methods for airway segmentation using confident airway volume, local change in segmentation volume, airway wall association, multi-scale topological and geometric leakage detection, forbidden volume insertion and freezing, and iterative shift-in-growing techniques starting with a conservative parameter/strategy and progressing toward generous ones along with post segmentation leakage removal. The systems and methods are fully automated, requiring no manual inputs or post-editing steps. The systems and methods use a region growing algorithm and iteratively grow an airway tree starting with an initial seed inside the trachea and a conservative region growing parameter value, e.g., the threshold value for simple intensity-based connectivity. During an iteration, the systems and methods execute the following sequential steps—(1) apply region growing from previously segmented confident airway volume without passing through any forbidden volume and identify leakages, if any, using segmented airway volumes at previous and current iterations, centerlines, local change in volume, airway wall association, scale and tortuosity; (2) identify the centerline and volume regions of the previous iteration that are associated with leakages in the initial rough segmentation of the current iteration, perform leakage correction to locate the exact leakage location within potential leakage region, and add forbidden volumes around the exact leakage location; and (3) shift the region growing parameter, e.g., the intensity threshold toward a more generous value for the next iteration. This iterative strategy of airway tree growing continues until the target threshold range is exhausted or a convergence occurs when the forbidden volume fills the boundary of the confident airway volume, i.e., no further region growing may happen. After iterative growing phase is complete, a final leakage removal strategy is used to remove any segmentation leakages. This embodiment presents two implementations (Implementations I and II) under the freeze-and-grow technology for airway segmentation. In this embodiment, two exemplary implementations of the technology are disclosed herein. Varying algorithms may be adopted to implement the following steps of the freeze-and-grow technology—(1) any preprocessing step to the CT image, (2) initial seed selection, (3) the choice of region growing and control parameter(s), (4) initial leakage detection and final leakage location and correction, (5) construction of the forbidden region, (6) termination criterion, and (7) final leakage pruning.

Also described herein are systems for computed tomography (CT)-based segmentation of airways comprising a CT scanning device, a network, and one or more networked computers. The CT scanning device provides an initial chest image that includes a trachea to at least one computer and the computer selects a seed in the trachea. The computer uses the seed to grow an airway region at a threshold that is the lowest CT intensity triggering a leakage. The computer identifies leakages using local change in segmentation volume, airway wall association, centerline morphology, topological and geometric features of centerline subtree and associated segmentation volume, scale and tortuosity analysis and an accurate location of leakage and leakage volume are identified. The leakage volume is removed, and the centerline is appropriately pruned and a forbidden volume is constructed around where the leakage originates. The networks computer then marks the marks the forbidden region as a frozen volume and no region growing or connectivity paths are allowed to pass through a forbidden region in subsequent iterations. In the next iteration, the leakage-free confident airway segmentation volume excluding the forbidden region is used as seeds for region growing with the next more generous region growing parameter.

Some of the methods described herein include a method for computed tomography (CT)-based segmentation of airways comprising providing a CT chest image including a trachea to a networked computer; selecting a seed inside the airway lumen, e.g., in the trachea; using the seed to grow an airway region at a region growing parameter that would just trigger a leakage; identifying the leakages using local change in airway volume, airway wall association along the boundary of the newly augmented airway volume in the initial rough segmentation at the current iteration, centerline morphology of the new airway volume, topological and geometric features of centerline subtree and associated segmentation volume, scale analysis along an airway centerline branch paths and a measure of distance-metric-based-tortuosity; accurate location of leakage; removing leakage volumes; pruning centerline branches; adding a forbidden volume around where the leakage originates.

Some of the methods described herein include a method for computed tomography (CT)-based segmentation of airways comprising providing a CT chest image including a trachea to a networked computer; selecting a seed in the trachea; applying a preprocessing step for airway tree enhancement, using the seed to grow an airway region at a threshold that would just trigger a leakage; identifying the leakages using local change in airway volume, airway wall association along the boundary of the newly augmented airway volume in the initial rough segmentation at the current iteration, centerline morphology of the new airway volume, topological and geometric features of centerline subtree and associated segmentation volume, scale analysis along an airway centerline branch paths and a measure of distance-metric-based-tortuosity; accurate location of leakage; removing leakage volumes; pruning centerline branches; adding a forbidden volume around where the leakage originates.

Also provided herein are images of airways created by the methods and systems described herein. These images are useful for among other things visualizing and analyzing the health and status of an airway system, providing unique airway phenotypes and differentiating subgroups of individuals within broad categories such as individuals with COPD, asthma, cystic fibrosis and other lung diseases involving the airway tree. Moreover, these images can be created at various time intervals for an individual patient and compared to each other. Variations in the images from one image to another can indicate relative health of the airway system, disease progression and the like.

Several leakage detection methods have been applied for CT-based airway segmentation. B. van Ginneken, W. Baggerman, and E. M. van Rikxoort, "Robust segmentation and anatomical labeling of the airway tree from thoracic CT scans," in International Conference on Medical Image Computing and Computer-Assisted Intervention, 2008, pp. 219-226: Springer. Tschirren et al. used topological features for leakage detection; specifically, they used the criterion that a leaked volume includes complex topological features, e.g., tunnels. P. K. Saha and B. B. Chaudhuri, "3D digital topology under binary transformation with applications," Computer vision and image understanding, vol. 63, no. 3, pp. 418-429, 1996. Others have used geometric rule-based approaches for leakage detection for airway tree segmentation.

The systems and methods described herein are innovative approaches of leakage detection using local change in segmentation volume, airway wall association along the boundary of the newly augmented airway volume in the initial rough segmentation at the current iteration, centerline morphology of the new airway volume, topological and geometric features of centerline subtree and associated segmentation volume, scale analysis along airway centerline paths and a measure of distance-metric-based-tortuosity to detect various types of leakages. E. Bullitt, G. Gerig, S. M. Pizer, W. Lin, and S. R. Aylward, "Measuring tortuosity of the intracerebral vasculature from MRA images," *IEEE transactions on medical imaging*, vol. 22, no. 9, pp. 1163-1171, 2003. Moreover, the iterative airway segmentation algorithm applied by the systems and methods introduces a unique notion of forbidden volume insertion strategy to progressively shift the segmentation strategy from a conservative to a generous region growing parameter (e.g., intensity threshold) scheme. The algorithm requires no threshold-related parameter. During an iteration, the intensity threshold or other parameter used for region growing is automatically computed to barely cause a leakage in the airway segmentation.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 5A shows an initial confident airway volume (CAV) (GREEN) segmentation using region growing approach; the centerline is shown in BLUE;

FIG. 5B shows a leakage (the WHITE blobby region at the lower-right part of the airway tree) at the next generous threshold value that includes several branches of CAV from the previous iteration; augmentation of valid airway branches in the current iteration are also shown in WHITE. The potential leakage region is marked in YELLOW;

FIG. 5C shows the results after leakage correction where the exact leakage root within the leakage region is computed (shown in PINK). This procedure is conducted to recover any valid airway volume within the potential leakage region.

FIG. 10A shows exemplary diagrams of detection of a spongy leakage using tortuosity of an airway centerline branch in accordance with an embodiment of the invention in which the tortuosity of each centerline path (between black points) checked in a breadth-first manner. A centerline branch with a high tortuosity is located (geodesic length: red, Euclidean distance: blue); and FIG. 10B shows exemplary diagrams of detection of a spongy leakage using tortuosity of an airway centerline branch in accordance with an embodiment of the invention in which the centerline paths and their descendants removed during leakage correction;

FIG. 11A shows exemplary results of airway tree segmentation using the new iterative multi-scale leakage detection algorithm in accordance with an embodiment of the invention after the first iteration;

FIG. 11B shows exemplary results of airway tree segmentation using the new iterative multi-scale leakage detection algorithm in accordance with an embodiment of the invention after the second iteration;

FIG. 11C shows exemplary results of airway tree segmentation using the new iterative multi-scale leakage detection algorithm in accordance with an embodiment of the invention after the third iteration; and FIG. 11D shows exemplary results of airway tree segmentation using the new iterative multi-scale leakage detection algorithm in accordance with an embodiment of the invention after the fourth iteration;

DETAILED DESCRIPTION OF THE EMBODIMENTS

Figure 1:
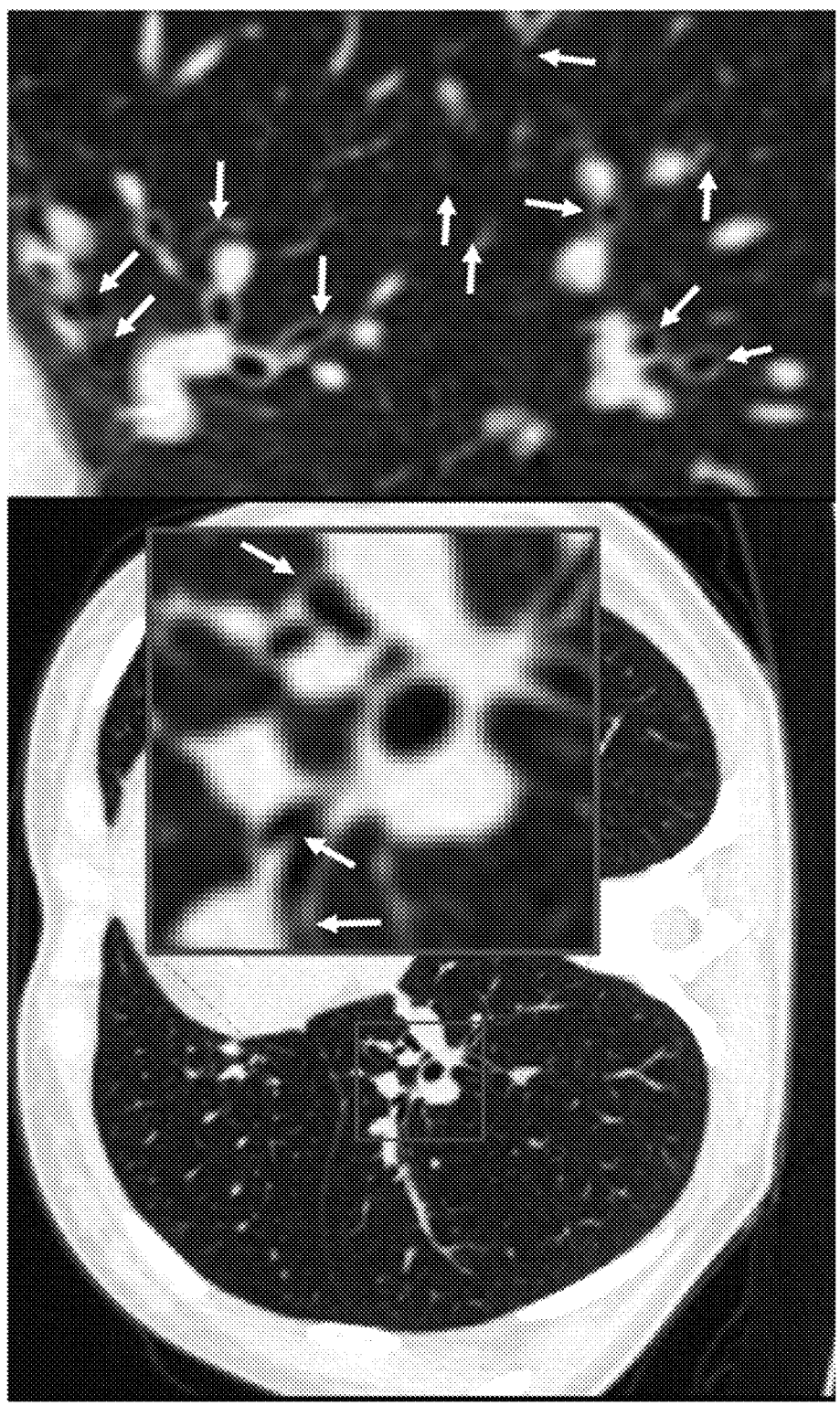
FIG. 1A shows an illustration of CT-based segmentation of airway trees. The figure shows reduced contrast of airway walls (indicated by white arrows) between airway and lung parenchyma due to noise and partial voxel volume. These low contrast airway walls are possible sites of leakages during segmentation. (Contrast settings: level=−450 HU, window=1200 HU)
FIG. 1B shows an illustration of CT-based segmentation of airway trees. The figure shows reduced contrast of airway walls (indicated by white arrows) between airway and lung parenchyma due to noise and partial voxel volume. These low contrast airway walls are possible sites of leakages during segmentation. (Contrast settings: level=−450 HU, window=1200 HU)
FIG. 1C shows an illustration of CT-based segmentation of airway trees. The figure shows reduced contrast of airway walls (indicated by white arrows) between airway and lung parenchyma due to noise and partial voxel volume. These low contrast airway walls are possible sites of leakages during segmentation. (Contrast settings: level=−450 HU, window=1200 HU)
Figure 2:
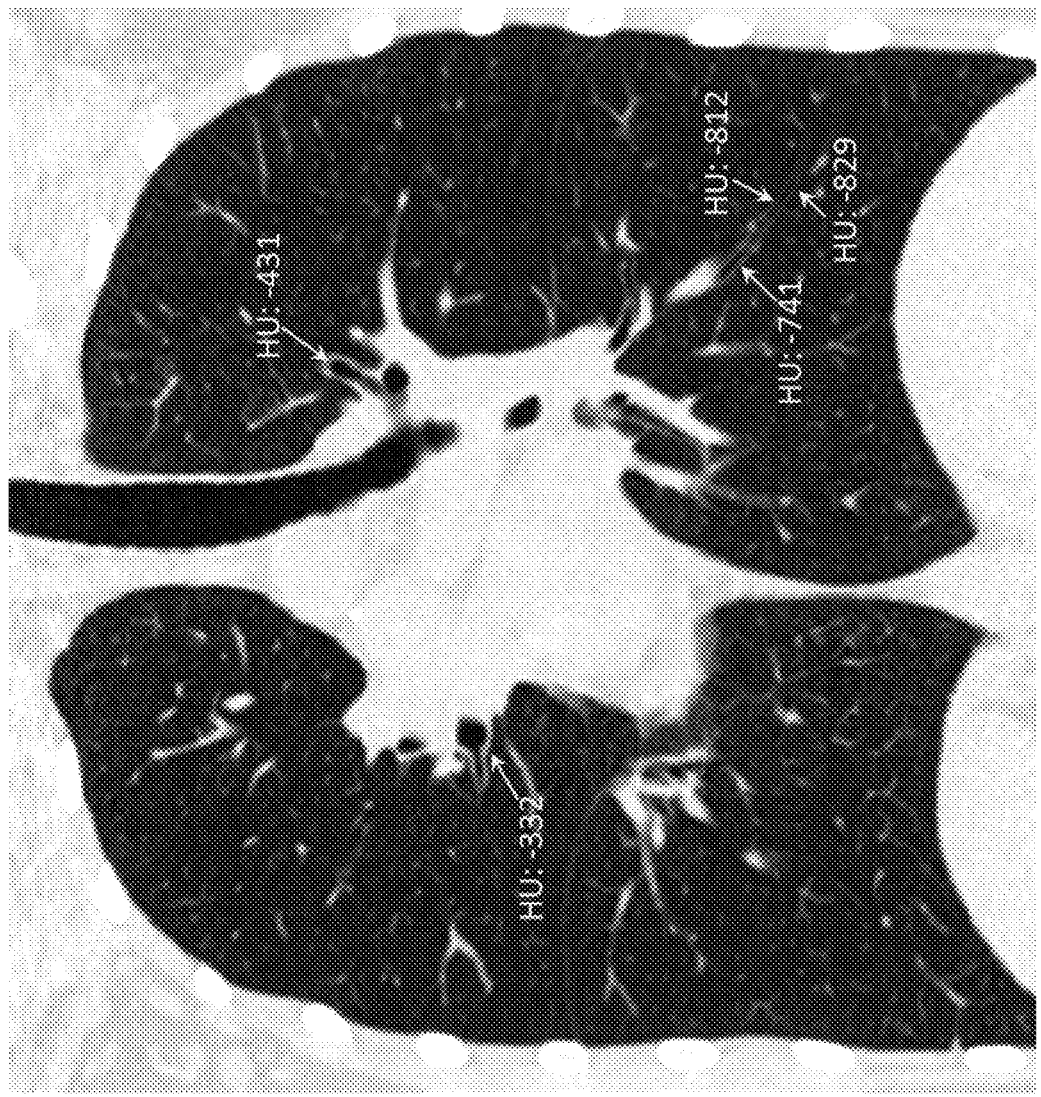
FIG. 2 shows CT values of airway walls at proximal and distal locations. Airway wall intensity values were reduced from −332 HU at a proximal location to as low as −829 HU at a distal location. (Contrast settings: level=−450 HU, window=1200 HU)

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the drawings.

Figure 3:
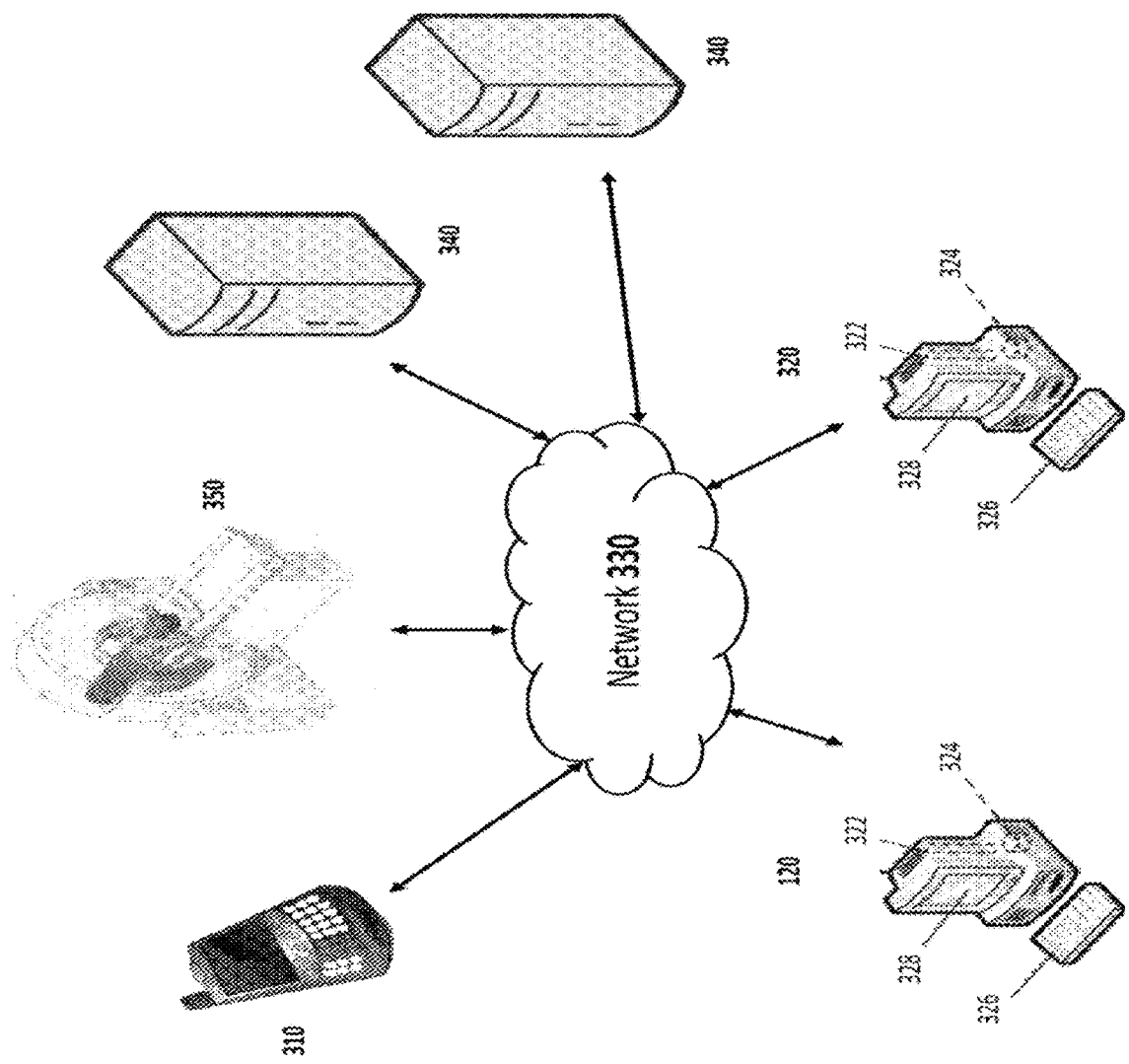
FIG. 3 shows exemplary hardware utilized by an embodiment of the invention.

The airway segmentation algorithm presented herein uses region growing-based segmentation together with new methods of confident airway volume and multi-scale topological and geometric leakage detection, detection of exact location of a leakage, leakage correction, and forbidden volume insertion and freezing techniques along with a gradual shift in region growing parameter/strategy to iteratively grow an airway tree in a chest CT image starting with an initial seed inside the airway lumen. The method is fully automated requiring no manual post-correction steps. FIG. 3 shows an exemplary layout of the hardware utilized by the invention. A block diagram of major steps of the algorithm is presented in FIG. 4. Also, schematic illustrations of results after different intermediate steps are shown in FIG. 5.

In the exemplary system 300, shown in FIG. 3, one or more peripheral devices 310 and a CT scanning device 350 are connected to one or more computers 320 through a network 330. Examples of peripheral devices 310 include smartphones, tablets, and wearable devices such as smartwatches. The network 330 may be a wide-area network, like the Internet, or a local area network, like an intranet. Because of the network 330, the physical location of the peripheral devices 310 and the computers 320 has no effect on the functionality of the hardware and software of the invention. Both implementations are described herein, and unless specified, it is contemplated that the peripheral devices 310 and the computers 320 may be in the same or in different physical locations. Communication between the hardware of the system may be accomplished in numerous known ways, for example using network connectivity components such as a modem or Ethernet adapter. The peripheral devices 310, the computers 320, and the CT scanning device 350 will include or be attached to communication equipment. Communications are contemplated as occurring through industry-standard protocols such as HTTP.

Each computer 320 is comprised of a central processing unit 322, a storage medium 324, a user-input device 326, and a display 328. Examples of computers that may be used are: commercially available personal computers, open source computing devices (e.g. Raspberry Pi), commercially available servers, and commercially available portable device (e.g. smartphones, smartwatches, tablets). In one embodiment, each of the peripheral devices 310 and each of the computers 320 of the system have software related to the system installed on it. In such an embodiment, data related to the patient studies performed are stored locally on the networked computers 320 or alternately, on one or more remote servers 340 that are accessible to any of the networked computers 320 through a network 330. In alternate embodiments, the software runs as an application on the peripheral devices 310.

Figure 4:
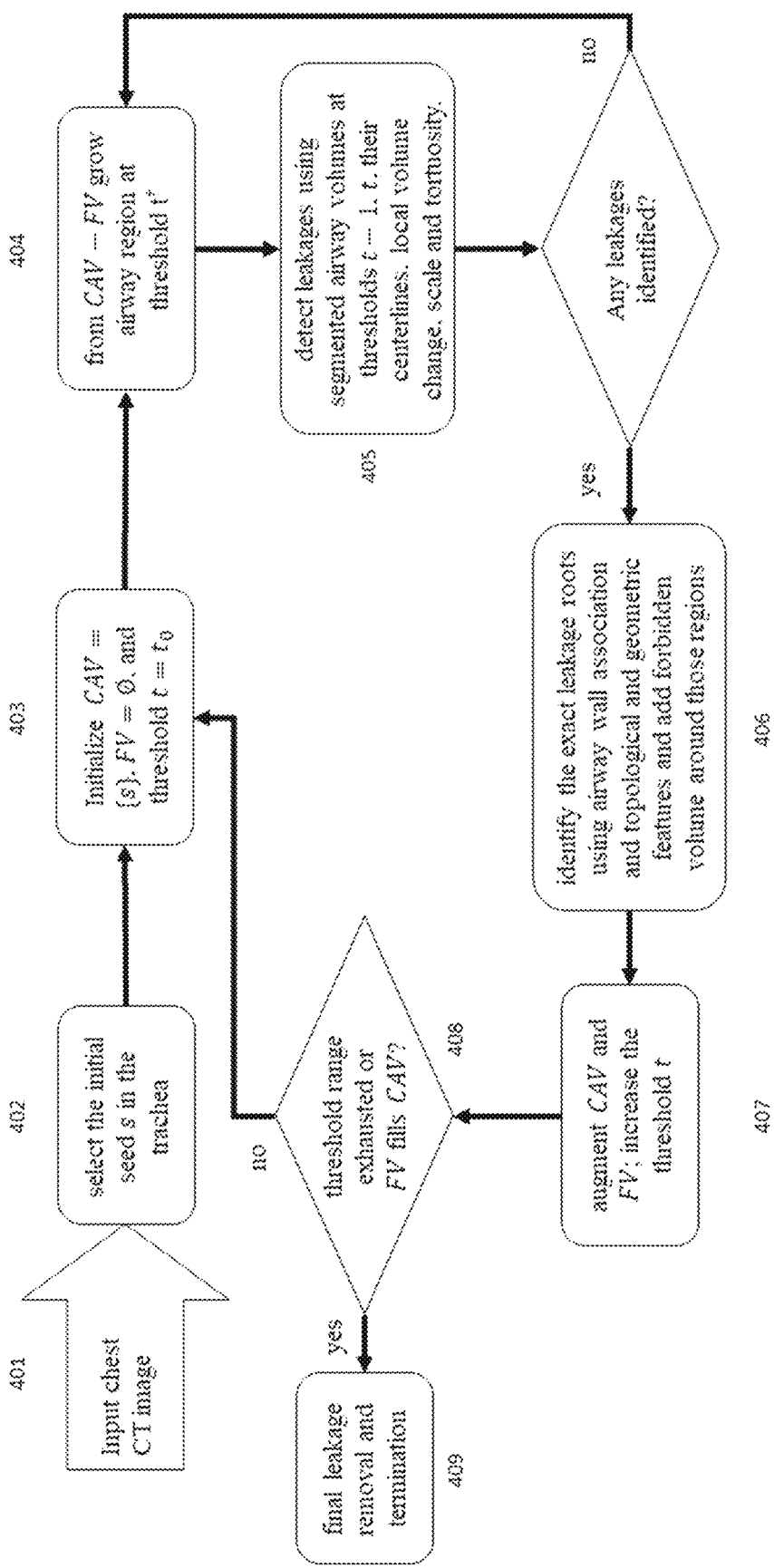
FIG. 4 shows an exemplary block diagram of major steps of the iterative algorithm of airway segmentation from human chest CT scans in accordance with an embodiment of the invention.
Figure 5:
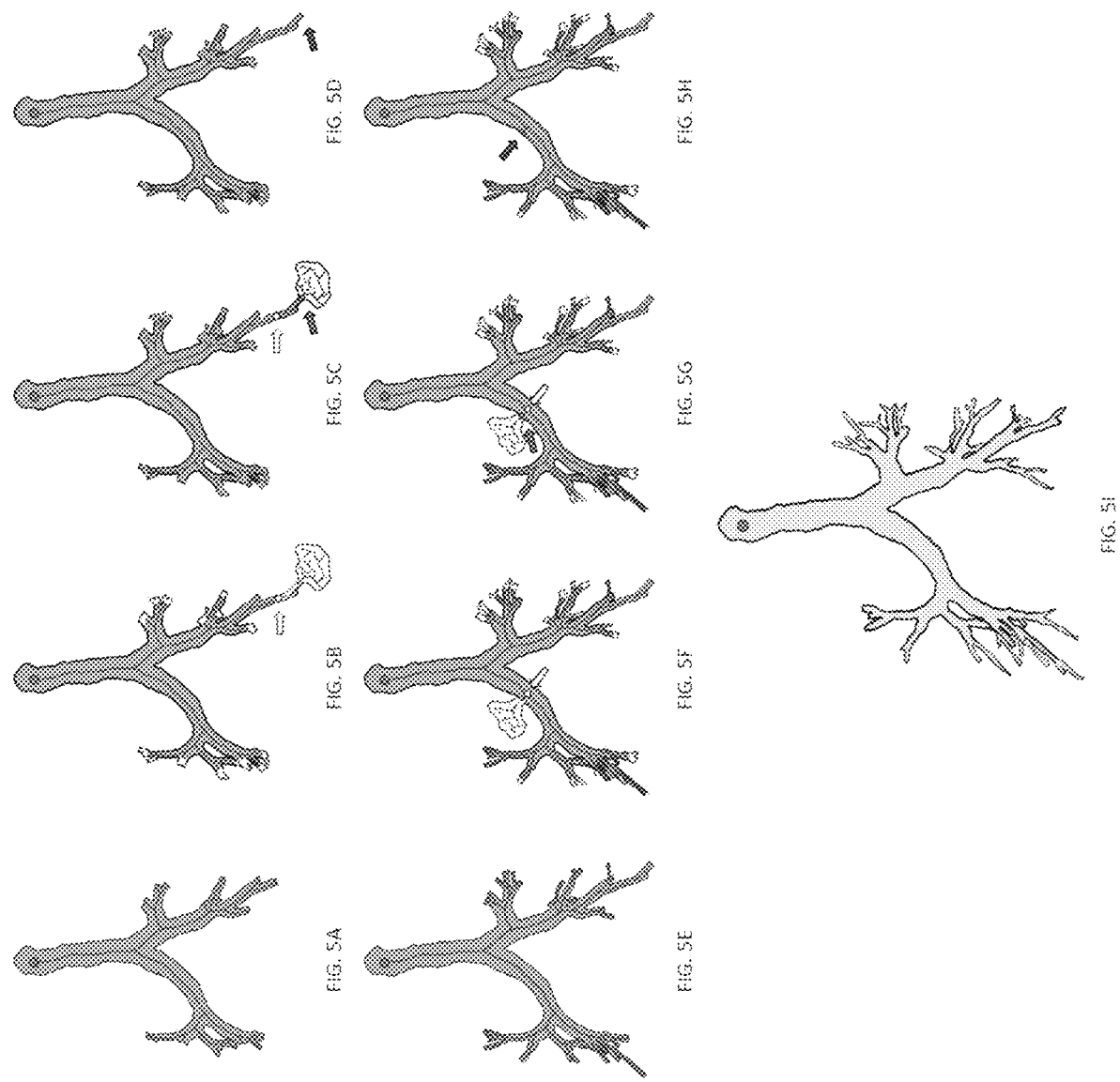
FIG. 5A shows an exemplary schematic description of the intermediate results of the airway segmentation algorithm in accordance with an embodiment of the invention. More specifically.
FIG. 5B shows an exemplary schematic description of the intermediate results of the airway segmentation algorithm in accordance with an embodiment of the invention. More specifically.
FIG. 5C shows an exemplary schematic description of the intermediate results of the airway segmentation algorithm in accordance with an embodiment of the invention. More specifically.
FIG. 5D shows a forbidden volume (FV) inserted around the valid airway volume adjacent to the leakage volume and is marked in RED; in subsequent iterations, region growing paths are not allowed to pass through a FV.
FIG. 5E shows the results of CAV and FV after a few more iterations.
FIG. 5F shows the segmentation results after the next iteration with a leakage (the WHITE out-pouch on the upper-left airway branch) extending out from the middle of a confident airway branch of the previous iteration with the potential leakage location marked in YELLOW.
FIG. 5G shows the results of leakage correction to identify the exact leakage location (marked in PINK)
FIG. 5H shows the results after leakage removal and insertion of a forbidden volume (RED)
FIG. 5I shows the results of CAV, i.e., the confident airway volume segmentation.

FIG. 4 is an exemplary block diagram of the algorithm applied by an embodiment of the invention. At step 401, the software of the present invention accepts input of a chest image from the CT scanning device 350. At step 402, the software automatically selects the initial seed in the airway lumen e.g. trachea. At step 403, the software of the invention initializes the confident airway volume (CAV), forbidden volume (FV), and the initial region growing parameter as a predefined value $t_0$. At step 404, the software uses CAV–FV as the seed to grow the airway tree $V_t$ using region growing at the threshold t. At step 405, the software detects leakages using segmented airway volumes at thresholds t and t−1, their centerlines ($S_t$ and $S_{CAV}$), local volume change, airway wall association, scale and tortuosity. If any leakages are found the process moves to step 406, else it returns to step 404 with an augmented setup of CAV=$V_t$ and $S_{CAV}$=$S_t$. During step 406, the software identifies the exact location and regions associated with leakages using airway wall association and multi-scale topological and geometric features of the centerline subtrees of each leakage region and their associated segmentation volumes. Using the augmented leakage-free CAV and its centerline at the threshold t, a forbidden volume FV is placed around the leakage location. At step 407, the software augments the regions corresponding to CAV and FV and the operating threshold value t is increased. At step 408, the software analyzes whether the entire range of threshold values has been exhausted or if a convergence has occurred where FV surrounds CAV. If so, a final leakage removal is applied, and the software process terminates, as shown at step 409. Otherwise, the software returns to step 404 of the process, repeating steps 404 through 408. This exemplary process is explained in further detail below.

Implementation I
Initialization

A seed voxel s is automatically detected inside the airway lumen, specifically, the trachea using an algorithm based on the approach taken by Mori et al. J. I. Hasegawa, J. I. Toriwaki, H. Anno, and K. Katada, "Recognition of bronchus in three-dimensional X-ray CT images with applications to virtualized bronchoscopy system," in *Pattern Recognition,* 1996., Proceedings of the 13th International Conference on, 1996, vol. 3, pp. 528-532: IEEE. Other automatic seed selection algorithms may be used in this step. The method applies compactness and size analysis of connected air-space in the upper quartile of axial slices in an acquired chest CT scan to locate the trachea. The seed is located at the centroid of the trachea. This step is marked in FIG. 4 as 402.

Throughout the iterative growth phase of the algorithm, two different volume regions are maintained—(1) the confident airway volume CAV, representing the region which has already been segmented as part of the airway tree, and (2) the forbidden volume FV, representing regions excluded for any connectivity path to enter since leakages have previously occurred through these regions. Upon initialization, s is the only voxel in the confident airway volume, i.e., CAV={s}; the forbidden volume is initialized as an empty set, i.e., FV=Ø. This step is marked in FIG. 4 as 403.

Region Growing-Based Segmentation

At the beginning of each iteration, the method applies a region growing-based segmentation approach to compute the initial segmentation from the confident airway volume i.e. CAV over I−FV, where I denotes the 3-dimensional (3-D) image space of the chest CT scan. The initial threshold value is automatically selected as the lowest parameter value, e.g. CT intensity, triggering an airway segmentation leakage. This step is marked in FIG. 4 as 404. The results of initial segmentation are illustrated in FIG. 5B, which includes apparent leakages together with several valid airway branches.

Next a post-processing step is performed on the initial rough segmentation volume to remove unwanted topological features such as holes and tunnels in the airway volume which may result in region-based segmentation. A fuzzy distance transform (FDT)-based closing algorithm is used to morphologically smooth the segmented volume, while accounting for partial voxel effects and avoiding artificially merging different regions through airway walls. Let the initial airway tree segmentation at a parameter value t be $V_t$, the closing operation is accomplished using the following membership function computed at each voxel $$p \in V_t, \mu(p) = 1 - e^{-\frac{(f(p)-\bar{f}(p))^2}{2\sigma^2}},$$

where f(p) is the CT intensity value at p, and $\bar{f}$(p) is the CT intensity at the voxel in $V_t$ closest to p. The values σ=50 HU and the FDT threshold of 0.25 voxel unit for closing were used for all experiments. After the closing operation, cavities inside the closed volume $V_t$ are filled using connected component analysis of I–$V_t$.

Centerline Computation

The leakage detection and correction of the process is based branch analysis of airway tree skeleton. The method by Palágyi is used for efficient computation the centerline of the segmented airway volume. K. Palágyi, "A Sequential 3D Curve-Thinning Algorithm Based on Isthmuses." In *International Symposium on Visual Computing*. Springer, Cham, 2014. The skeleton computed using this method often contains spurious noisy branches, which cause difficulty in characterizing leakage regions in subsequent steps. An effective method is used for pruning spurious skeletal branches in a curve skeleton using skeletal subtree depth and local scale. The skeletal subtree emanating from a skeletal voxel immediately following a junction voxel is checked for its spuriousness. Specifically, let p be a skeletal voxel immediately following a junction voxel; the skeletal subtree emanating from p is marked as a spurious, if the ratio of depth(p)/scale(p) is below a threshold. It is expected that for valid airway centerline branches, this ratio would be high. One of ordinary skill in the art would readily understand that other centerline computation algorithms and pruning methods may also be used to accomplish this step.

Leakage Detection

The next crucial step of the method is determining whether any leakages have occurred when growing at the current region growing parameter value as indicated as step 405. The leakage detection step is accomplished in two stages—(1) initial detection of potential leakage locations and (2) confirmation of leakages. Potential leakages are identified by analysis of local change in volume, airway wall association, centerline morphology, scale and a geodesic distance-based measure of tortuosity along centerline paths of the initial rough segmentation of airway tree at the current iteration, while the segmented airway volume and its skeletal tree's morphology is used for confirmation of a leakage.

Local change in airway volume at the current iteration is determined using the airway segmentation volumes CAV of the previous iteration, the initial rough segmentation of airway $V_t$ at the current iteration, and their centerlines $S_{CAV}$ and $S_t$, respectively. For a given centerline voxel p∈$S_{CAV}$, its associated volume $f_t(p)$ in $V_t$ is computed as the number of voxels in $V_t$ whose nearest centerline voxel is p; the associated volume $f_{CAV}(p)$ of p in CAV is defined similarly. For a voxel p∈$S_{CAV}$, let the associated volume $f_t(p)$ denote the number of voxels in $V_t$ whose nearest skeletal voxel in $S_{CAV}$ is p. The value of $f_t(p)|p \in S_{CAV}$ are computed using a distance transform and nearest neighbor propagation algorithm from $S_{CAV}$. Finally, the subtree following a skeletal voxel p∈$S_{CAV}$ is marked as a potential leakage if $f_t(p)-f_{CAV}(p)$ exceeds as threshold value. Smoothing of the value $f_t$ and $f_{CAV}$ can be separately applied along the paths of the centerline representation $S_{CAV}$. At a leakage location, the change in local segmentation volume between iterations is expected to be high. This is used to locate potential leakage locations. Either a change is skeletal volume or airway segmentation volume may be used to detect potential leakages.

If no potential leakage regions are found, the algorithm returns to step 404 with an increased threshold value, CAV=$V_t$, and $S_{CAV}=S_t$. If potential leakage regions are found, the tree-morphological features of $V_t$ and $S_t$ are used to confirm a leakage. Specifically, a leakage at a voxel p∈$S_{CAV}$ is confirmed if the following condition related to volume-to-average depth ratio VDR(p) holds: VDR(p)/(π·scale²(p))>$α_{VDR}$, where VDR(p) is the ratio of the associated volume to the average depth of the skeletal subtree $X_p$ following p. The associated volume of $X_p$ may be defined as $\Sigma_{q \in X_p} f_t(q)$. The average depth of the skeletal subtree $X_p$ following p is the average geodesic length from p to each end voxel of $X_p$. The equation is designed to model an airway branch as a tubular structure, and the term on the 1. h. s. of the inequality gets a value of '1' when the structure is a cylinder. Also, note that the numerator captures volume per unit subtree length, while the denominator represents the cross-sectional area. It is important to mention that the value of VDR(p) is computed using $V_t$ as the airway tree volume and its skeleton $S_t$.

Leakage Correction

Figure 6:
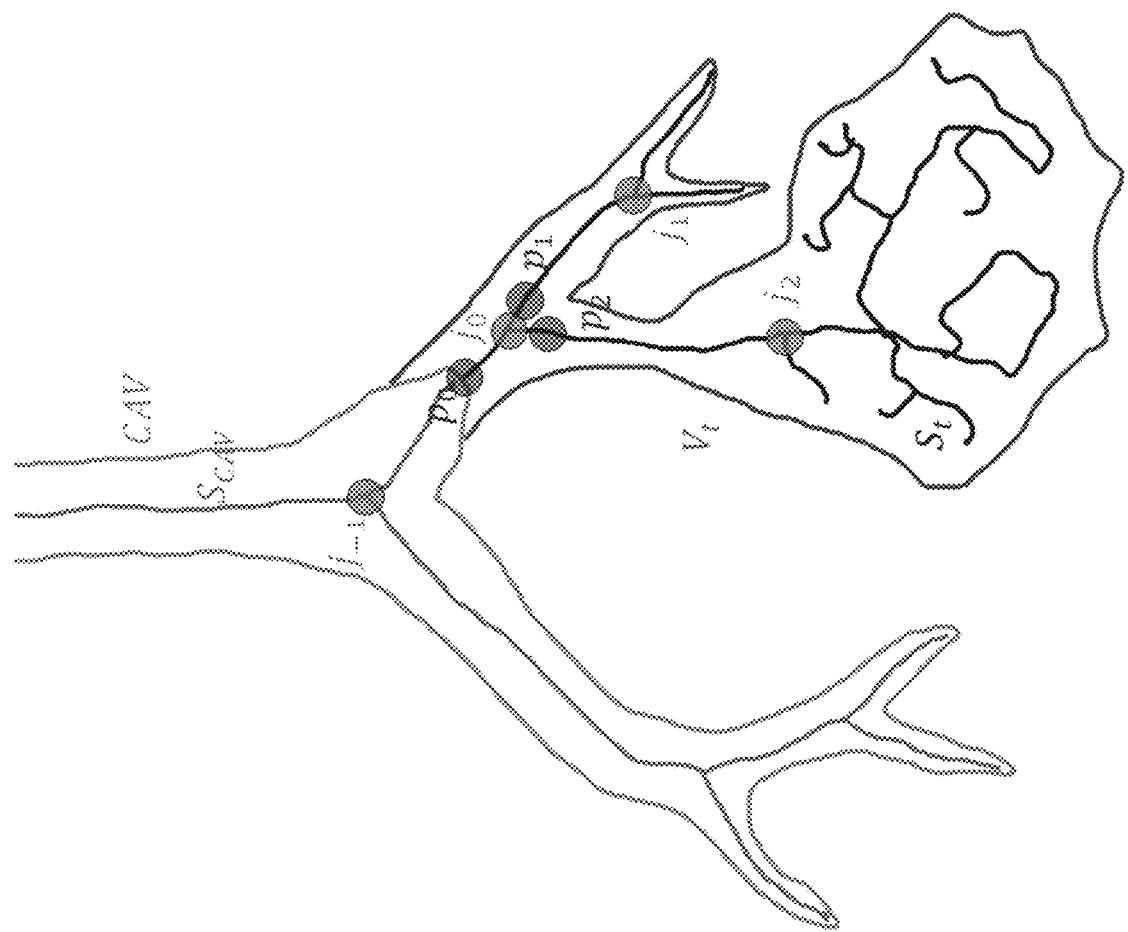
FIG. 6 shows a schematic representation of the leakage correction process. Confident airway volume CAV (GREEN), it skeleton $S_{CAV}$ (GRAY), initial rough segmentation volume at current iteration $V_t$ (RED), and its skeleton $S_t$ (BLACK). Initial potential leakage location $p_0$ (BLUE). Junctions marked $j_i$ are shown in PINK.

The leakage correction strategy is applied to find the exact leakage root and maximally extend the airway tree to recover any valid airway regions part of the potential leakage region (as shown in 406). In FIG. 6, an example is shown where the potential leakage at $p_0$ contains valid airway tree volume as well as a leakage volume. The accurate location of a leakage root is determined by using a tree traversal approach to check branch segment validity. The tree traversal algorithm is initiated from each skeletal voxel where a leakage is confirmed. Let $p_0$ be the initial leakage location, tree-traversal based accurate leakage location algorithm works as follows—(1) identify the branch b containing $p_0$, (2) if the branch b is not valid, mark $p_0$ as a leakage location and terminate, else if b is a terminal branch, terminate, else, find the immediate follower junction j, for each neighbor $p_i$ of j on a following skeletal branch recursively call Algorithm 5 with $p_i$ as the root voxel. For example, the neighbors $p_1$ and $p_2$ for the junction $j_0$ in FIG. 6.

The leakage root is located using the following three features: (1) forward-branch-length, (2) airway wall association, and (3) volume-to-average length ratio of a branch. Note that, the skeleton of an airway segmentation volume must be represented as a tree despite the presence of tunnels.

Given the tree representation of an airway skeleton, the forward-branch-length of a skeletal voxel p∈$S_t$ is the longest among the Euclidean length of the branch containing p and those of the immediate child-branches. For example, FIG. 6, forward-branch-length of $p_0$ is the maximum of the Euclidean lengths of the branches $j_{-1}j_0$, $j_0j_1$, and $j_0j_2$.

Figure 7:
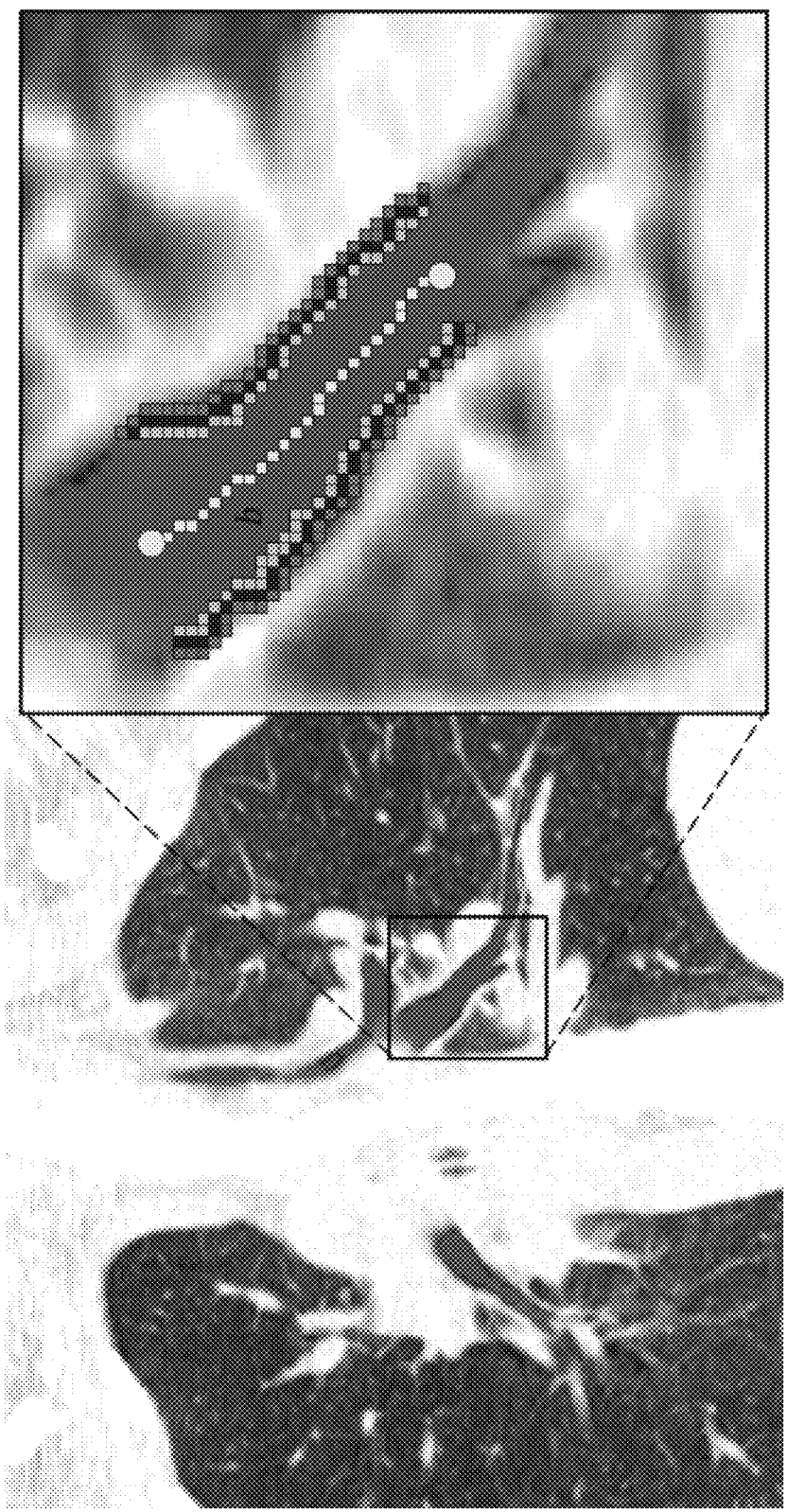
FIG. 7 shows the computation of airway wall association of a skeletal branch b shown in yellow for a 2-dimensional CT slice. (CT contrast settings: level −450 HU, window 1200 HU)

The airway wall association of a skeletal branch is computed using an airway wall model in CT imaging as follows: a dark tubular structure, i.e., airway lumen, surrounded by a bright boundary or airway wall. Let us consider a boundary voxel p of the segmentation volume V. The boundary of p, denoted by B(p), is the set of all background 6-neighbors of p. To account for partial volume effect, B(p) is radially augmented to $B_{aug}(p)$ as $B_{aug}(p)=B(p)\cup\{2\ q-p|q\in B(p)\}$, where "2q–p" denotes the voxel two units away from p along the direction from p to q. This augmentation process is illustrated in FIG. 7 in 2-D, where cyan represents boundary pixels, while those in blue and magenta are the 6-neighbors and radially augmented pixels. The airway wall association at p is defined as $$AWA(p) = e^{-\frac{(f_{aug}(p)-\mu)^2}{2\sigma^2}},$$

where $f_{aug}(p)$ is the intensity of the brightest voxel in $B_{aug}(p)$, and $\mu$ and $\sigma$ are the expected mean and standard deviation of airway wall intensity. The airway wall association of a branch is computed as the fractional count of its boundary voxels with AWA(•)>0.6; the threshold value was determined experimentally over augmented neighborhoods of manually selected valid branches.

Finally, a skeletal branch is valid if it satisfies the following three conditions related to—(1) airway wall association is greater than 0.7, (2) the forward-branch-length is greater than half of the average airway branch length at the same generation as determined empirically, and (3) scale-normalized volume-to-average length ratio is less than 3.

The last step of leakage correction is to augment the confident airway volume CAV and its skeleton $S_{CAV}$. First, the valid airway tree skeleton $S_{CAV}$ of the previous iteration is expanded within $S_t$ using tree traversal, where expansions along individual skeletal paths are terminated if a leakage location is faced or a terminal voxel is reached. Finally, CAV is expanded as: $CAV = \cup_{p \in S_{CAV}} f_{t(p)}$, where $f_{t(p)}$ is the set of voxels of $V_{t(p)}$ that are closer to p than any other voxel in $S_{CAV}$. Note that when augmenting CAV, the updated version of $S_{CAV}$ is used.

Volume Freezing

Figure 8A:
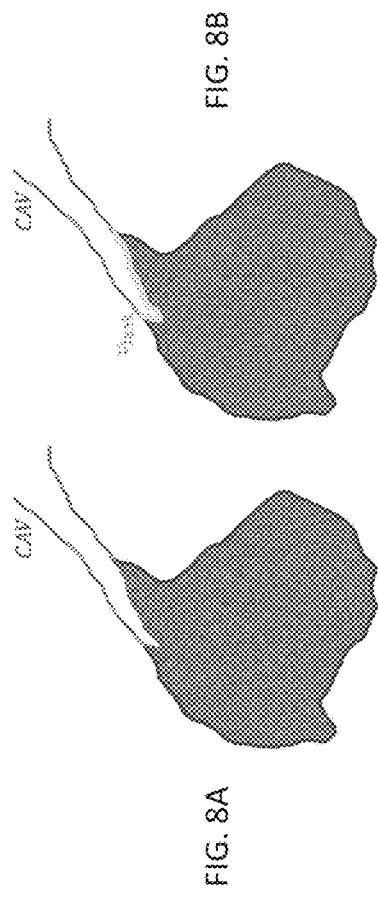
FIG. 8A shows a schematic description of the volume freezing process in which the augmented confident airway volume CAV and the adjacent leakage volume (gray) after leakage detection and correction.
Figure 8B:
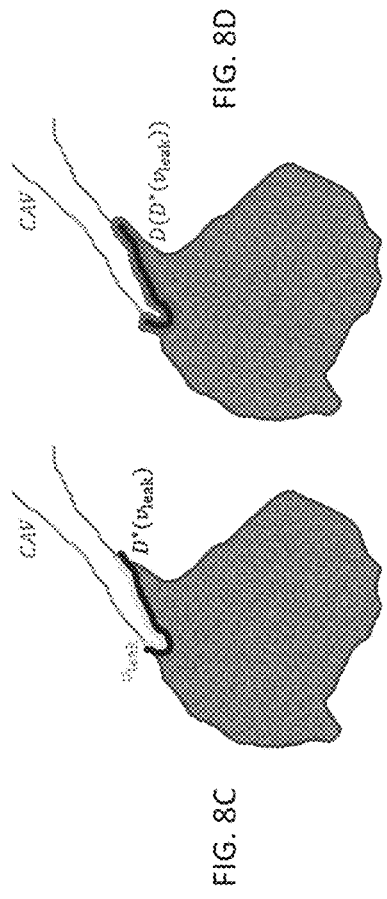
FIG. 8B shows a schematic description of the volume freezing process in which the leakage boundary $v_{leak}$ in YELLOW.
Figure 8C:
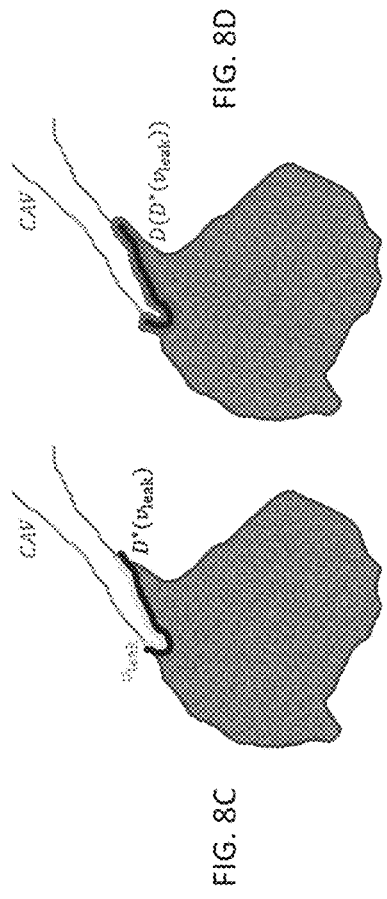
FIG. 8C shows a schematic description of the volume freezing process in which the initial restricted dilation of $v_{leak}$ in BLUE.
Figure 8D:
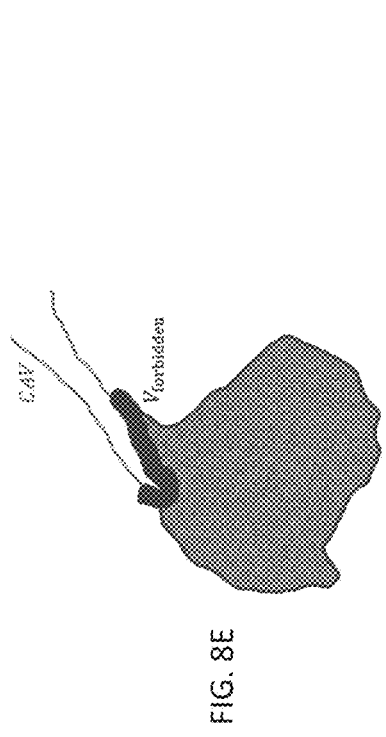
FIG. 8D shows a schematic description of the volume freezing process in which the dilation of the result of FIG. 8C in PINK.
Figure 8E:
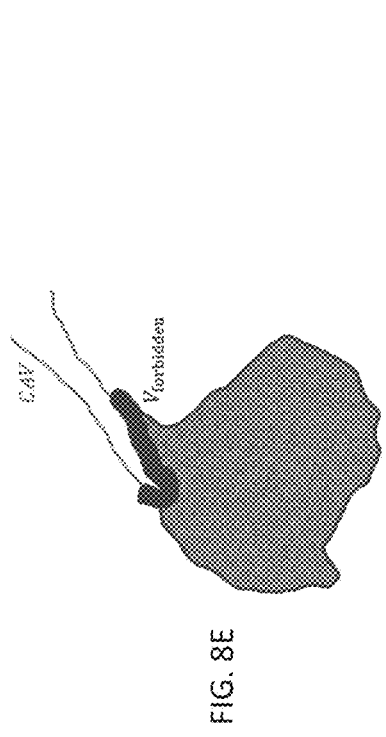
FIG. 8E shows a schematic description of the volume freezing process in which the corresponding forbidden region for the leak shown in FIG. 8A in PURPLE.

After augmenting the confident airway volume CAV, volume freezing is applied around each leakage site. This procedure places a protection layer around the leakage site and connectivity paths are not allowed to pass through these regions in subsequent iterations. This is done by augmenting the forbidden volume FV. First, the leakage boundary of CAV, denoted as $V_{leak}$, is computed as the set of voxels in CAV that are 6-adjacent to $V_T$-CAV (FIG. 8B). A forbidden volume is inserted around $V_{leak}$ as follows: $V_{forbidden} = \cup_{p \in V_{leak}} D_3(D_5^*(p))$, where a restricted dilation $D_5^*$ of 5×5×5 is applied over $V_T$-CAV to expand the forbidden patch along the boundary of CAV (FIG. 8C), while an unrestricted dilation $D_3$ is applied to add a protection layer inside CAV (FIG. 8D). Finally, the total forbidden region FV is augmented as $FV = FV \cup V_{forbidden}$. This forbidden volume after the current iteration is considered as a frozen region, and no connectivity paths in subsequent iterations can enter it. This step 407 is crucial for developing an iterative-parameter-shift strategy starting with a conservative parameter (e.g., intensity threshold) and progressing toward more generous values.

Setup for Next Iteration

During each iteration of the new airway segmentation algorithm, the algorithm augments the airway tree, and adds forbidden volumes wherever leakages are detected. The leakage detection and correction step, described herein, produces leakage-free confident volume of airway tree along with forbidden volumes. In the next iteration, region growing starts from the confident airway volume excluding the forbidden volumes and the connectivity paths are prohibited from entering into forbidden volumes. The forbidden volume is crucial to arrest leakages through the volume predisposed to leakages while segmenting forward tree branches at a more generous threshold. Finally, the iterative phase of the process terminates when the target threshold range is exhausted, or a convergence occurs, i.e., the forbidden volume fills the entire confident airway volume after an iteration.

This step is crucial to design a strategy of iteratively shifting the threshold intensity value starting with a conservative one and then progressing towards more generous threshold values.

After locating all leakages, pruning those, and inserting forbidden volumes through steps 405-408, the augmented setup of CAV, $S_{CAV}$, and FV, enters the next iteration with a more generous threshold value if a termination condition is not occurred. In the next iteration, region growing starts from the confident airway volume excluding the forbidden volumes and the connectivity paths are prohibited from entering into forbidden volumes. This iterative process continues until the target threshold range is exhausted or a convergence occurs, i.e., the forbidden volume surrounds the entire confident airway volume after an iteration.

Final Pruning

Once the iterative segmentation phase of the process is complete, a final leakage removal is applied on the segmented airway tree volume to remove any small segmentation leakages which may have avoided the leakage detection criteria during the iterative phase of the method. To detect and remove such leakages a combination of topological and geometric features and intensity characteristics of the segmentation volume, its corresponding centerline, and the underlying CT image are used. A support vector machine (SVM)-based classifier based on topological and geometric features extracted from the centerline representations of manually notated leakages from a training set is used for this purpose. Features used include branch length (of branch, parent, and children), subtree volume (skeletal and airway tree), branching angle (parents, children), generation, terminal branch status, branch intensity, subtree depth, maximum subtree depth. The centerline of the segmented airway volume generated using the iterative phase of the process and its associated features are computed and passed through the classifier. The airway volumes associated with centerline regions classified as leakages are subsequently removed. Variations of final punning step can be developed using variations of machine learning, neural network, deep learning, or artificial intelligence methods.

An alternate approach for final leakage removal uses a deep learning approach to develop 3-dimensional U-net classifier to remove leakage regions. The 3-D U-net classifier is provided the original chest CT image and the airway tree segmentation result from the iterative phase of the method. This convolutional neural network-based framework is used to generate a probability map of whether a segmented airway tree voxel is a leakage or not. This probability map may be thresholded to remove voxels which are classified as having a high probability of being a leakage This deep learning-based classification system is trained using chest CT scans, segmentation volumes with leakages and a ground truth of the manually corrected leakage-free segmentations.

Implementation II

Initial Rough Segmentation

The algorithm presented here uses simple intensity-based region growing to compute an initial rough segmentation of the airway tree volume. Such an initial segmentation is only a rough estimation, which may include one or more leakages. Two major requisites in this step are—(1) identification of seed points and (2) determination of the intensity threshold value. As discussed herein, only one seed is used in the first iteration, which is automatically located inside the trachea using the algorithm by K. Mori, J.-i. Hasegawa, J.-i. Toriwaki, H. Anno, and K. Katada, "Recognition of bronchus in three-dimensional X-ray CT images with applications to virtualized bronchoscopy system," in *Pattern Recognition, 1996., Proceedings of the 13th International Conference on,* 1996, vol. 3, pp. 528-532: IEEE. In a subsequent iteration, confident airway volume excluding the forbidden volumes located during the previous iteration are used as seeds for region growing; the method of locating confident airway volume and forbidden volume are further described herein.

During an iteration, airway segmentation volume is grown from confident airway volume excluding the forbidden volumes. The threshold value for airway region growing is automatically selected as the lowest intensity value triggering a segmentation leakage. For efficient computation of the optimum threshold, a binary search process between t and t+$\Delta_{max}$ is performed. For all experiments presented herein, a value of 300 HU is used as $\Delta_{max}$. It should be noted that the final threshold value is independent of the choice of $\Delta_{max}$.

It was noted that, often, the intensity-based region-growing algorithm leaves small tunnels and cavities inside the segmented region. These cavities and tunnels are filled using a mathematical morphological closing operation with a structure element of 5×5×5. This step is imperative to ensure that an initial segmented volume does not contain small holes which would add significant errors in the leakage detection and correction processes which use centerline computation, scale analysis, tortuosity estimation, and other topological and geometric features of the centerline and its associated airway volume. After filling small tunnels and cavities, the initial rough segmentation is passed to the next module for leakage detection.

Leakage Detection

The leakage detection method 405 presented herein is based on analysis of final segmentation of airway volume after previous iteration, the initial segmentation of airway volume at the current iteration, centerlines of segmented airway volumes, local change in airway volume, airway wall association, scale and distance metric-based tortuosity along airway centerline branches. As described herein, during an iteration, initial rough segmentation of an airway volume is computed from the confident airway volume excluding the forbidden volumes; let $V_t$ be the initial rough segmentation of airway volume. First, a centerline tree is computed for $V_t$ with the initial seeds on the trachea as the root using a robust and efficient centerline detection algorithm recently developed by Jin et al. D. Jin, C. Chen, and P. K. Saha, "Filtering non-significant quench points using collision impact in grassfire propagation," in *International Conference on Image Analysis and Processing,* 2015, pp. 432-443: Springer. The centerline detection method uses fuzzy distance transform (FDT) and collision-impact based centered minimum cost paths to locate individual centerline branches. P. K. Saha, F. W. Wehrli, and B. R. Gomberg, "Fuzzy distance transform: theory, algorithms, and applications," *Computer Vision and Image Understanding,* vol. 86, no. 3, pp. 171-190, 2002. Other centerline detection algorithm may be used to accomplish this step.

The leakage detection method 405 generates a partially ordered representation of centerline branches. Let $(\pi_1, \pi_2, \ldots, \pi_n)$ be the breadth-first traversal of the partially ordered centerline tree, where $\pi_i$ is a centerline branch, and $\cup_i \pi_i$ represents the entire centerline tree. Individual centerline branches are examined for leakages in the order of their breadth-first traversal. If a leakage is detected on a centerline branch $\pi_i$, the exact leakage point p on the branch is located and it is pruned up to that point. Moreover, the centerline branches descendant to point p are removed from the center tree. Centerline branches are examined for several types of leakages—(1) rapid leakages without associated airway wall, (2) centerline morphology-based leakages, (3) solid leakages, and (4) spongy leakages. The methods for detecting these two specific types of leakages are described below.

Rapid leakages without associated airway wall are identified by first locating a region, say $S_i$, on the airway centerline obtained from the previous iteration, which show large increase in associated airway volume after the initial rough segmentation of the current iteration. The volume $V_i$ associated with $S_i$ is analyzed for leakage detection. Each airway path volume B within the volume $V_i$ is analyzed for airway wall association. A branch with the percent of airway wall association falling below a threshold (e.g., 70%) is marked as a leakage branch.

Figure 9A:
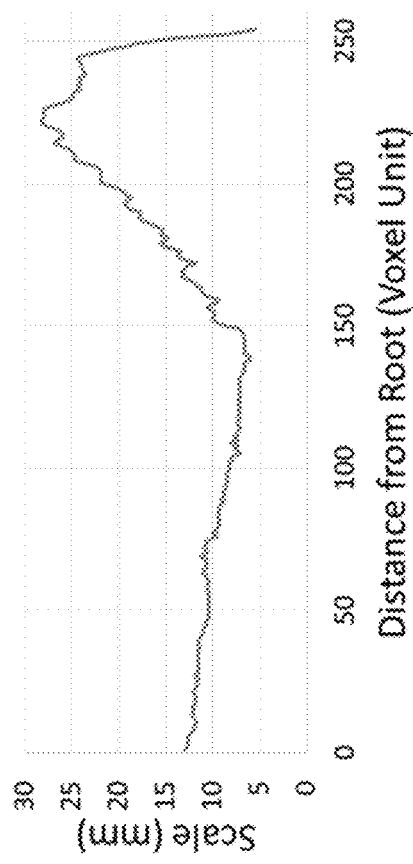
FIG. 9A shows exemplary detection of a solid leakage using scale analysis along an airway centerline path in accordance with an embodiment of the invention in which an initial rough segmentation of an airway tree with a solid leakage where the centerline path for current checking of leakages is shown in red.
Figure 9B:
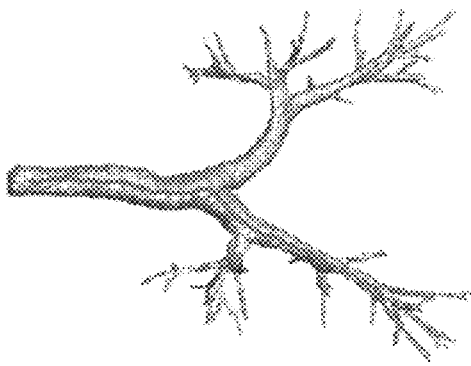
FIG. 9B shows exemplary detection of a solid leakage using scale analysis along an airway centerline path in accordance with an embodiment of the invention in which there is a computed scale profile along the centerline path.
Figure 9C:
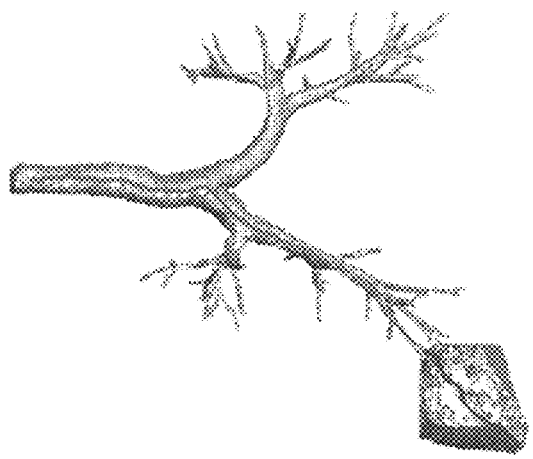
FIG. 9C shows exemplary detection of a solid leakage using scale analysis along an airway centerline path in accordance with an embodiment of the invention in which there is leakage detection on the median filtered scale profile.

Centerline morphology-based leakages are located by analyzing the length and orientation of a specific centerline branch and its distal centerline subtree. Solid leakages are characterized by rapid scale inflation along an airway centerline path. In general, local scales along an airway tree path are quasi-non-increasing in the proximal-to-distal direction. Thus, a solid leakage can be detected by locating sudden increases in scale values along an airway centerline path. This process is illustrated in FIG. 9. The scale at a centerline voxel on a skeletal path is computed using a star-line approach which determines the length of the shortest object intercept through the centerline voxel. Y. Liu et al., "A robust algorithm for thickness computation at low resolution and its application to in vivo trabecular bone CT imaging," *IEEE Transactions on Biomedical Engineering,* vol. 61, no. 7, pp. 2057-2069, 2014. Computed scale profile along a centerline path of FIG. 9A is shown in FIG. 9B. This computed scale profile is passed through a median filtering (window size=5) to smooth small, noisy dents and protrusions; the scale profile after smoothing is shown in FIG. 9C. The leakage detection algorithm is applied on the smoothened scale profile, and it works as follows.

Figure 9D:
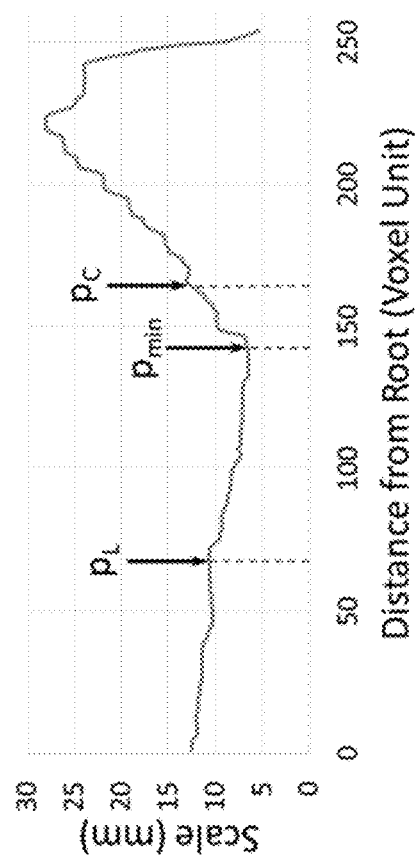
FIG. 9D shows exemplary detection of a solid leakage using scale analysis along an airway centerline path in accordance with an embodiment of the invention in which there is a leakage-corrected airway tree.

Let $p_c$ be a voxel on a centerline path $p_0, p_1, \ldots, p_{c-1} > p_c, p_{c+1}, \ldots$ The ratio between the scale at $p_c$ and that at each of its predecessor's $p_i \in p_0, p_1, \ldots, p_{c-1}$ is checked in the proximal-to-distal direction. A leakage on the branch is confirmed on the target branch at or prior to $p_c$ if a voxel $p_l(l<c)$ is found whose scale ratio with $p_c$ exceeds a predefined threshold value of 2. Finally, the exact location of leakage is detected by finding the minimum scale voxel $p_{min}$ on the centerline branch between $p_c$ to $p_l$ (see FIG. 9C), and the branch is pruned up to $p_{min}$. Final results after leakage detection and correction are shown in FIG. 9D.

After a centerline path is checked for solid leakages, it is further checked for spongy leakages. Such leakage regions contain tunnels and cavities which are not filled by the morphological closing operation on initial rough segmentation discussed above. Inside these regions, the centerline path propagates in an aimless and uncontrolled manner and the scale-analysis of solid leakage detection fails to detect such spongy leakages due to holes. To detect such leakages, we use distance metric tortuosity, defined as the ratio between the geodesic length and the Euclidean distance between end points of a centerline path. Normally, the Euclidean distance between the end points of the centerline of an airway branch is similar in value to its geodesic length. Due to meandering nature of centerline path in a spongy leakage, the geodesic length of a centerline segment increases rapidly as compared to the Euclidean distance between its end points. By applying a predefined threshold to the tortuosity of a centerline path, the systems and methods determine whether a centerline path is part of a spongy region and need to be pruned. This process is schematically described in FIG. 10.

Setup for Next Iteration

During each iteration of the new airway segmentation algorithm, the algorithm augments the airway tree, and adds forbidden volumes wherever leakages are detected. The leakage detection and correction step, described herein, produces leakage-free confident volume of airway tree along with forbidden volumes. In the next iteration, region growing starts from the confident airway volume excluding the forbidden volumes and the connectivity paths are prohibited from entering into forbidden volumes. The forbidden volume is crucial to arrest leakages through the volume predisposed to leakages while segmenting forward tree branches at a more generous threshold. Finally, the process terminates when the target threshold range is exhausted, or a convergence occurs, i.e., the forbidden volume fills the entire confident airway volume after an iteration.

Here, $V_{t-1}*$ denotes the leakage-free confident airway segmentation from the previous iteration. First, the volume, say $V_{i,t-i}$, within $V_{t-1}*$ associated with a leakage in the initial rough segmentation of the current iteration is determined. The leakage associated volume $V_{i,t-i}$, is dilated by a $(2m+1) \times (2m+1) \times (2m+1)$ structure element to construct a forbidden volume and no connectivity paths in subsequent iterations can enter inside the forbidden volume. This step is crucial to design a strategy of iteratively shifting the threshold intensity value starting with a conservative one and then progressing towards more generous threshold values. The dilation step is needed to stop connectivity paths from entering the narrow region (mostly including partial-volume voxels) between the segmented airway volume and the surrounding airway wall.

Example 1: Experimental Analysis

All experimental results presented in this section are derived using Implementation I.

The experiments were aimed to examine the branch-level accuracy of the new airway segmentation method at segmental levels, sub-segmental levels, and one level beyond. The method was applied on chest CT scans of fifteen normal non-smoking subjects (previously acquired under IRB approval; age: 21-48 Yrs., mean: 28.5 Yrs.; 7 female) at total lung capacity (TLC: 90% vital capacity) using a volume-controlled breath-hold maneuver. CT scans were acquired on a Siemens Definition Flash 128 (at 120 kV with effective mAs of 200), with images reconstructed at 0.5 mm slice thickness using a standard B35 kernel. Airway segmentation results on a CT image using the new method after different iterations are shown in FIG. 11.

Figure 12B:
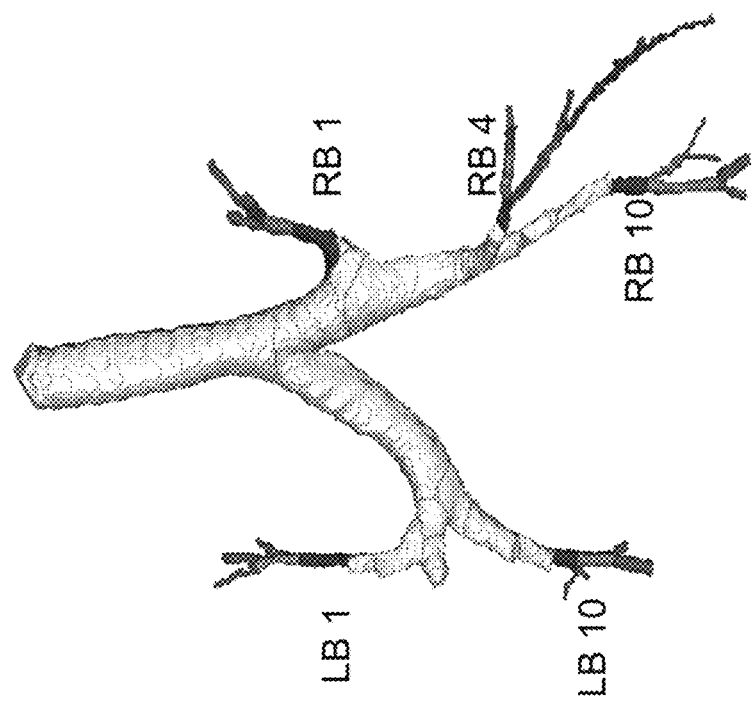
FIG. 12B shows experimental results of an airway tree representation in which there are five anatomic airway paths used in the experiments.
Figure 12A:
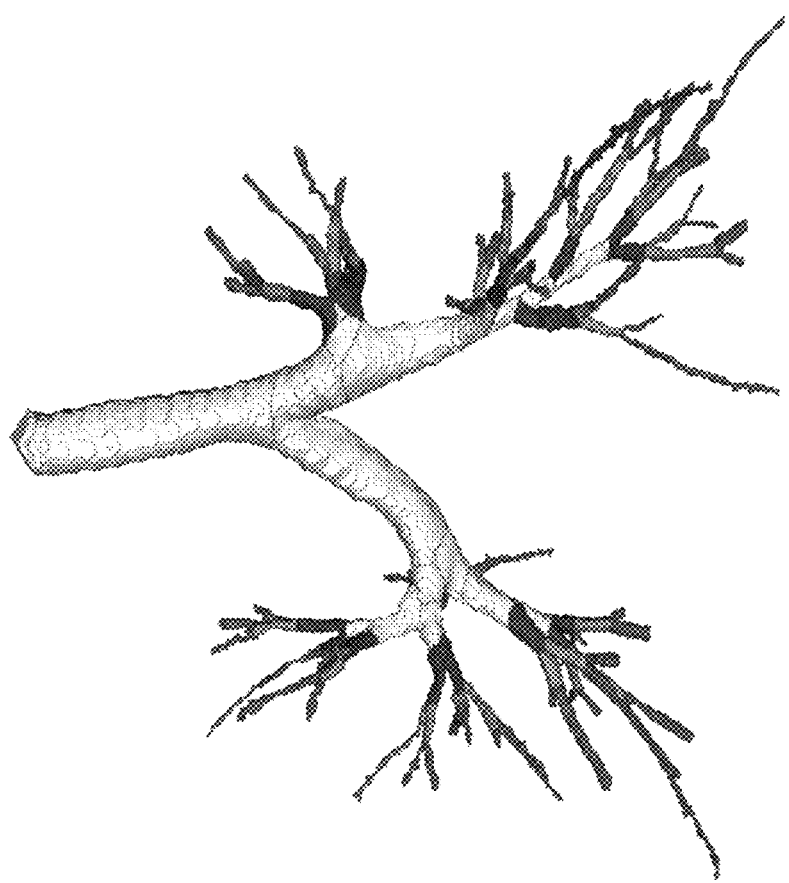
FIG. 12A shows experimental results of an airway tree representation in which there is an airway tree representation including segmental levels (red), sub-segmental levels (green), and one level beyond (pink)

For quantitative experiment, we examined the branch level accuracy of the new segmentation method along five standardized airway paths passing through segmental bronchial segments (RB1, RB4, RB10, LB1, LB10) and continuing two generations beyond these segmental bronchi. An airway tree up to segmental level and two-generations beyond is shown in FIG. 12A. Branches at segmental level and two-generations beyond along the five anatomic airway paths, used in our experiments, are shown in FIG. 12B.

To examine the branch-level accuracy of the new method, the method's segmentation results were compared with the matching airway segmentation results obtained by an expert user's manual editing (both removal of leakage volumes and addition of missing branches) on the airway segmentation results computed using the algorithm provided within the Apollo pulmonary workstation software (VIDA Diagnostics, Coralville, Iowa). During comparative examination, a blinded expert user compared every branch at the segmental level and two-generations-beyond along each of the five anatomic paths on 3-D visual representations of two airway segmentation results-one using the new method and the other using the manually edited one. No leakage was observed in the automatic segmentation results using the new method on any of the fifteen data sets used in this experiment. The new automatic method successfully detected all branches at the segmental level and two-generations-beyond, which were detected in the manually edited results along with no visual leakages.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention. All documents and patent applications cited herein are incorporated in their entireties by reference.

The invention claimed is:

1. A system for computed tomography (CT)-based segmentation of airways comprising a CT scanning device, a network, and one or more networked computers wherein the one or more networked computers:
   (a) apply region growing from a previously segmented airway volume in airways from a CT scan;
   (b) locate potential leakage locations in the airways;
   (c) detect exact leakage locations in the airways,
   (d) prune airway segmentation volumes beyond exact leakage locations in the airways;
   (e) generate a leakage-corrected segmentation of the airways; and
   (f) add one or more forbidden volumes associated with the individual leakages from the leakage-corrected segmentation of the airways.

2. The system of claim 1, wherein the one or more networked computers perform one or more additional iterations of all of steps (a)-(f).

3. The system of claim 2, wherein the one or more networked computers freeze forbidden volumes for the additional iterations.

4. The system of claim 2, wherein the one or more networked computers shift a segmentation parameter toward a more generous value for the additional iterations.

5. The system of claim 4, wherein the segmentation parameter is a threshold value.

6. The system of claim 2, wherein no additional iterations are performed when a target threshold is exhausted or a convergence occurs.

7. The system of claim 6, wherein a convergence occurs when no additional region growing can be applied.

8. The system of claim 6, wherein the one or more networked computers perform a final leakage removal strategy to remove segmentation leakages in the airways.

9. The system of claim 8, wherein the final leakage removal strategy applies a three-dimensional U-net classifier.

10. The system of claim 8, wherein the final leakage removal strategy applies a deep learning classifier.

11. The system of claim 8, wherein the final leakage removal strategy applies a machine learning classifier.

12. The system of claim 1, wherein one seed is used to initiate region growing at step (a).

13. The system of claim 1, wherein steps (b) and (c) involve one or more of the following:
   (1) volume to average depth ratio of segmented volume subtree representing a unique measure of pseudo cross-sectional area of a subtree;
   (2) forward branch length; or
   (3) airway wall association.

14. A method for computed tomography (CT)-based segmentation of airways comprising the steps of:
   (a) applying region growing from a previously segmented airway volume in airways from a CT scan;
   (b) locating potential leakage locations in the airways;
   (c) detecting exact leakage locations in the airways,
   (d) pruning airway segmentation volumes beyond exact leakage locations in the airways;
   (e) generating a leakage-corrected segmentation of the airways; and
   (f) adding one or more forbidden volumes associated with the individual leakages from the leakage-corrected segmentation of the airways.

15. The method of claim 14, further comprising performing one or more additional iterations of all of steps (a)-(f).

16. The method of claim 15, further comprising freezing forbidden volumes for the additional iterations.

17. The method of claim 15, further comprising shifting a segmentation parameter toward a more generous value for the additional iterations.

18. The method of claim 17, wherein the segmentation parameter is a threshold value.

19. The method of claim 15, wherein no additional iterations are performed when a target threshold is exhausted or a convergence occurs.

20. The method of claim 19, wherein a convergence occurs when no additional region growing can be applied.

21. The method of claim 19, further comprising performing a final leakage removal strategy to remove segmentation leakages in the airways.

22. The method of claim 21, wherein the final leakage removal strategy applies one of a three-dimensional U-net classifier, a deep learning classifier or a machine learning classifier.

23. The method of claim 14, wherein one seed is used to initiate region growing at step (a).

24. The method of claim 14, wherein steps (b) and (c) involve one or more of the following:
   (1) volume to average depth ratio of segmented volume subtree representing a unique measure of pseudo cross-sectional area of a subtree;
   (2) forward branch length; or
   (3) airway wall association.

\* \* \* \* \*